United States Patent [19]

Umezawa et al.

[11] 4,049,497
[45] Sept. 20, 1977

[54] PRODUCTION OF ANTIBIOTICS NEOTHRAMYCIN A AND NEOTHRAMYCIN B

[75] Inventors: Hamao Umezawa; Tomio Takeuchi, both of Tokyo; Masa Hamada, Hoya; Shinichi Kondo, Yokohama; Masaaki Ishizuka; Hiroshi Naganawa, both of Tokyo, all of Japan

[73] Assignee: Zaidan Hojin Biseibutsu Kagaku Kenkyu Kai, Japan

[21] Appl. No.: 747,470

[22] Filed: Dec. 6, 1976

Related U.S. Application Data

[60] Division of Ser. No. 659,319, Feb. 19, 1976, which is a continuation-in-part of Ser. No. 556,985, March 10, 1975, abandoned.

[30] Foreign Application Priority Data

Mar. 12, 1974 Japan .................................. 49-2767
Oct. 15, 1975 Japan .............................. 50-123256

[51] Int. Cl.$^2$ ........................................ C12D 13/9/14;
[52] U.S. Cl. ............................ 195/80 R; 260/239.3 T;
260/326.5 B
[58] Field of Search ............... 195/80 R, 96; 424/119;
260/326.5 B, 239.3 T

[56] References Cited

U.S. PATENT DOCUMENTS 3,074,855   1/1963   Okuda et al. ...................... 195/80 R

OTHER PUBLICATIONS

Yamamoto et al., "Streptomyces Antibiotic B-15645," *Chemical Abstracts,* vol. 73, No. 21, p. 252, Abs. No. 108248h (1970).
Shorin et al., "Antibacterial and Antitumor properties of Antibiotic 6613," *Chemical Abstracts,* vol. 56, (May), Abs. No. 12249e.
Zaretskii et al., "Effect of some Anticancer Antibiotics on mouse leukemia," *Chemical Abstracts,* vol. 56, (May), Abs. No. 12276e.
Shirling et al., "Cooperative Description of Type Strains of Streptomyces," *International Journal of Systematic Bacteriology,* vol. 22, No. 4, p. 323 (1972).
Brazhnikova et al., "Sibiromycin : Isolation and Characterization" *Journal of Antibiotics,* vol. 25, No. 11, pp. 668–673 (1972).
Nishioka et al., "Mode of Action of Tomaymycin," *Journal of Antibiotics,* vol. 25, No. 11, pp. 660–667 (1972).
*Japan Medical Gazette,* vol. 8, No. 4, pp. 5–6 (Apr. 1971).
*Japan Medical Gazette,* vol. 6, No. 2, p. 15 (Feb. 1969).
Furumai et al., "Studies on Cycloheximide–Producing Strains," *J. Antibiotics* (B), (Tokyo), vol. 17, (1964), pp. 181–189.
Igarashi et al., "Fermicidin, A New Antibiotic Active Against Yeast and Trichomonas," *J. Antibiotics* (B), (Tokyo), vol. 7, (1954), pp. 221–225.
Shirling et al., "Cooperative Description of Type Cultures of Streptomyces Species Descriptions from First Study," *International Journal of Systematic Bacteriology,* vol. 18, (1968), p. 122.
Mesentse et al., "Structure of Sibiromycin," *Journal of Antibiotics,* vol. 27, No. 11, pp. 866–873 (1974).

*Primary Examiner*—Raymond N. Jones
*Assistant Examiner*—Thomas G. Wiseman
*Attorney, Agent, or Firm*—Herbert W. Taylor, Jr.

[57] ABSTRACT

There are disclosed two new antibiotics formerly denominated MC916-A and MC916-B and now called neothramycin A and neothramycin B which are potent inhibitors of the growth of leukemia cells, e.g. Leukema L-1210 cells in mice. They are produced by controlled fermentation of Streptomyces FERM-P 2452 (A.T.C.C. 31123).

21 Claims, 4 Drawing Figures

PRODUCTION OF ANTIBIOTICS NEOTHRAMYCIN A AND NEOTHRAMYCIN B

CROSS-REFERENCE TO RELATED APPLICATIONS

This application is a division of our prior, copending application Ser. No. 659,319 filed Feb. 19, 1976 which in turn was a continuation-in-part of prior, copending application Ser. No. 556,985 filed Mar. 10, 1975 and now abandoned.

BACKGROUND OF THE INVENTION

This invention relates to chemical compounds produced by fermentation and used to inhibit the growth of leukemia cells.

SUMMARY OF THE INVENTION

This invention relates to two new antibiotics which each exhibit a high activity inhibitory to the growth of leukemia cells and are useful as anti-tumor agents but exhibit low antibacterial activity. More particularly, this invention relates to the new antibiotics formerly designated MC916-A substance and MC916-B substance, respectively, and now designated neothramycin A and neothramycin B, respectively, and also to a process for the production of these new antibiotics by cultivation of a strain of Streptomyces. This invention also relates to the recovery and purification of these specific new antibiotic substances and to their use for pharmaceutical purposes.

Hereinafter, by the term neothramycin is meant neothramycin A or neothramycin B or their mixture unless otherwise stated.

Some antibiotics which are useful as anti-tumor agents for the therapeutic treatment of leukemia, for example, are daunomycin, adriamycin, etc. In an attempt to obtain further new anti-tumor agents of antibiotic type, we collected various soil samples, isolated microorganism from such soil samples and investigated metabolic products which are produced by the aerobic cultivation of the isolated microorganisms. We isolated a new microorganism from a soil sample collected in the grounds of Biseibutsu Kagaku Kenkyu-sho in Shinagawa-ku, Tokyo, Japan, and we have designated this newly isolated microorganism as MC916-C4 strain. It has been confirmed that this MC916-C4 strain belongs to the genus Streptomyces. We have now found that two new antibiotics having a low antibacterial activity but high activity inhibitory to the growth of leukemia L-b 1210 cells in mice and to the growth of a certain kind of tumor cells are produced and accumulated in the culture broth of the MC916-C4 strain. We have now succeeded in isolating these new antibiotics from the culture broth and designated them as neothramycin A and neothramycin B, respectively.

An object of this invention is to provide new substances which are useful as anti-tumor agents. Another object of this invention is to provide the neothramycin A and neothramycin B, either alone or in mixture thereof as new and useful anti-tumor agents. A further object of this invention is to provide a process for the preparation of the neothramycin A and neothramycin B by cultivation of the MC916-C4 strain. Other objects of this invention will be clear from the following descriptions.

According to one aspect of this invention, there is provided as a new antibiotic substance, neothramycin having an activity inhibitory to the growth of leukemia L-1210 cells in mice and a low antibacterial activity, said substance having an acidic function; being soluble in methanol, ethanol, propanol, chloroform and dioxane and slightly soluble in water but sparingly soluble or substantially insoluble in ethyl ether and n-hexane; being positive to Rydon-Smith reaction and red tetrazolium reaction, weakly positive to ninhydrin reaction but negative to Ehrlich reaction and Sakaguchi reaction; giving essentially only carbon, hydrogen, nitrogen and oxygen upon elemental analysis thereof; exhibiting a relative mobility of said substance to alanine (1.0) being 0.17 on high-voltage filter paper electrophoresis (3500 volts, 35 minutes) using formic acid-acetic acid-water (25:75:900 by volume) as an electrolyte solution; said substance being at least one member selected from the group consisting of neothramycin A and neothramycin B;

a. said neothramycin A being further characterized by giving C, 57.46%, H, 5.76%, N, 9.84% and the remainder oxygen upon elemental analysis thereof; giving a molecular weight of 250 to 300 as measured by Barger-Akiya method; having an infrared absorption spectrum pelleted in potassium bromide corresponding to that shown in FIG. 1 of the attached drawings and characterized by absorption peaks at 3450, 2950, 1630 (shoulder), 1600, 1510, 1460, 1440, 1410, 1280, 1200, 1180, 1120, 1080, 1010, 870, 790 and 760 cm$^{-1}$; having ultraviolet absorption spectra corresponding to those shown in FIG. 3 of the attached drawings characterized by absorption maxima at 223 nm ($E_{1\ cm}^{1\%}$ 855), 240 nm (shoulder), 265 nm ($E_{1\ cm}^{1\%}$ 290) and 318 nm ($E_{1\ cm}^{1\%}$ 156) in a solution thereof in 10% water-methanol, by absorption maxima at 223 nm ($E_{1\ cm}^{1\%}$ 885), 240 nm (shoulder) 265 nm ($E_{1\ cm}^{1\%}$ 290) and 320 nm ($E_{1\ cm}^{1\%}$ 139) in a solution thereof in N/10 HCl-methanol (1:9) and by absorption maxima at 228 nm ($E_{1\ cm}^{1\%}$ 635), 254 nm ($E_{1\ cm}^{1\%}$ 566), 291 nm ($E_{1\ cm}^{1\%}$ 422) and 324 nm ($E_{1\ cm}^{1\%}$ 412) in a solution thereof in N/10 NaOH-methanol (1:9); and giving an $R_f$ value of 0.57 in thin layer chromatography on silica get with chloroform-methanol (10:1 by volume) as the developing solvent; and b. said neothramycin B being further characterized by giving C, 57.00%, H, 5.58%, N, 9.75% and the remainder oxygen upon elemental analysis thereof; giving a molecular weight of 250 to 300 as measured by Barger-Akiya method; having an infrared absorption spectrum pelleted in potassium bromide corresponding to that shown in FIG. 2 of the attached drawings and characterized by absorption peaks at 3400, 2960, 1630 (shoulder), 1600, 1510, 1440, 1400, 1280, 1200, 1080, 1010, 990, 940, 870, 790 and 760 cm$^{-1}$; having ultraviolet absorption spectra corresponding to those shown in FIG. 4 of the attached drawings and characterized by absorption maxima at 224 nm ($E_{1\ cm}^{1\%}$ 935), 240 nm (shoulder), 265 nm (shoulder) and 318 nm ($E_{1\ cm}^{1\%}$ 167) in a solution thereof in 10% water-methanol (1:9), by absorption maxima at 224 nm ($E_{1\ cm}^{1\%}$ 1000), 240 nm (shoulder), 265 nm (shoulder) and 320 nm ($E_{1\ cm}^{1\%}$ 156) in a solution thereof in N/10 HCl-methanol (1:9) and by absorption maxima at 228 nm ($E_{1\ cm}^{1\%}$ 800), 254 nm ($E_{1\ cm}^{1\%}$ 725), 291 nm ($E_{1\ cm}^{1\%}$ 456) and 324 nm ($E_{1\ cm}^{1\%}$ 466) in a solution thereof in N/10 NaOH-methanol (1:9); and giving an $R_f$ value of 0.50 in thin layer chromatography on silica gel with chloroform-methanol (10:1 by volume) as the developing solvent.

This invention embraces neothramycin A and neothramycin B substances, either alone or in a mixture of them, which may be present in a dilute solution, as a crude concentrate, as a crude solid, as a purified solid, as the free acid form and in the form of a salt thereof with a metal or an organic amine. Neothramycin A has been obtained as a colorless powder which has no definite melting point, melts gradually near 105° C. and decomposes at 132°-147° C. with foaming and which exhibits a specific optical rotation $[\alpha]_D^{26} = +272°$ (C 0.52, dioxane). From the results of elemental analysis and the determination of molecular weight, it is probable that neothramycin A has an empirical formula $C_{13}H_{14}N_2O_4 \cdot \frac{1}{2}$ ane (1:1 in volume) at room temperature for one hour followed by column chromatography on silica gel gives neothramycins A and B in a good yield.

From these data, neothramycins A and B are isomers which are convertible into each other and belong to the anthramycin group of antibiotics possessing a benzodiazepine structure. They are distinguished from anthramycin, dextrochrysin and sibiromycin by their UV spectra. The UV spectra of tomaymycin and neothramycins are very similar but they are different in their molecular formulae and other spectra.

TABLE 1

| Proton | PMR Chemical Shifts of Neothramycins and Their Methyl Derivatives | | | |
|---|---|---|---|---|
| | Neothramycin A | Neothramycin B | Methylneothramycin A | Methylneothramycin B |
| $CH_2 \times 2$ | 1.7-2.5 | 1.7-2.5 | 1.8-2.6 | 1.8-2.6 |
| $OCH_3$ | | | 3.28 s | 3.44 s |
| CH | 3.80 m | 3.78 m | 3.72 m | 3.80 dd |
| arom. $OCH_3$ | 3.90 s | 3.88 s | 3.90 s | 3.88 s |
| OH | 5.00 d | 5.10 d | | |
| CH | 5.69 dd | 5.78 m | 5.56 d | 5.35 dd |
| arom. H | 6.70 s | 6.69 s | 6.75 s | 6.64 s |
| arom. H | 7.43 s | 7.40 s | 7.48 s | 7.36 s |
| CH | 7.62 d | 7.70 d | 7.73 d | 7.54 d |
| phenol OH | 8.00 s | 7.98 s | 8.04 s | 7.94 s |

Chemical shifts, δ (ppm) were measured in deuterodioxane using TMS as the internal reference.

$H_2O$. This formula has been confirmed by high-resolution mass-spectrometry (Found: m/e 262.0934, Calcd. mol. wt. for $C_{13}H_{14}N_2O_4$ 262.0952). The ultra-violet absorption spectrum of neothramycin A in an alkaline solution exhibits a shift towards the longer wave length as shown in FIG. 3. As shown in Table 1, NMR spectrum of neothramycin A shows the presence of 14 protons. Neothramycin B is very similar in its properties to neothramycin A and has been obtained as a colorless powder which has no definite melting point, commences to decompose at 144° C. with foaming and completely melts at 151° C. and which exhibits a specific optical rotation $[\alpha]_D^{26} = +314°$ (C 0.48, dioxane). Neothramycin B has the empirical formula: $C_{13}H_{14}N_2O_4 \cdot 1\frac{7}{8}$ $H_2O$. This formula has been confirmed by high-resolution mass-spectrometry (Found: m/e 262.0939, Calcd. mol. wt. for $C_{13}H_{14}N_2O_4$, 262.0952). The ultraviolet absorption spectrum of neothramycin B in an alkaline solution exhibits a shift towards the longer wave length, as shown in FIG. 4. As shown in Table 1, NMR spectrum of neothramycin B shows the presence of 14 protons, similarly to neothramycin A. Neothramycin A and B are stable for a long period of time when stored in the form of a solid powder thereof in a cold and dark place.

But, neothramycin A and B are unstable in 50% aqueous ethanol of pH 2.5 and the activities are reduced to 25% and 22%, respectively, at room temperature for 16 hours. In 50% aqueous ethanol of pH 6.5 or pH 8.0 at room temperature for 16 hours, 80-90% activity of neothramycin A and 70-80% activity of neothramycin B remain, but an equilibrium conversion of neothramycin A to B or B to A is shown by thin-layer chromatographic analysis. Neothramycin A or B is easily converted to a mixture of methyl-neothramycins A [$R_f$ 0.71 on silica gel thin-layer chromatogram with chloroform-methanol (10:1 volume)] and B ($R_f$ 0.61) in anhydrous methanol at room temperature for 16 hours. Methylneothramycin A is crystallized from a mixture of acetone and benzene, colorless microcrystals, m.p. 137°-140° C. (dec.); $[\alpha]_D^{26}$ +640° (C, 0.24, dioxane), MS, m/e 276.1089 (Calcd. mol. wt. for $C_{14}H_{16}N_2O_4$, 276.1108). Methylneothramycin B is obtained as a colorless powder, m.p. 61°-69° C. (dec.); $[\alpha]_D^{26}$ +778° (C, 0.22, dioxane), MS, m/e 276.1071. UV spectra of methylneothramycins are similar to those of neothramycins and the PMR chemical shifts are shown in Table 1. Mild hydrolysis of methylneothramycin A or B in 0.01N HCl-dioxane By structural studies, the following structures have been submitted by the inventors for neothramycin A ($R^1$ = OH, $R^2$ = H), neothramycin B ($R^1$ = H, $R^2$ = OH), methylneothramycin A ($R^1$ = $OCH_3$, $R^2$ = H) and methylneothramycin B ($R^1$ = H, $R^2$ = $OCH_3$).

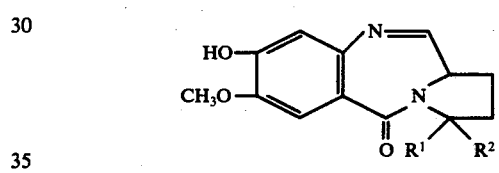

Referring to the attached drawings.

Figure 1:
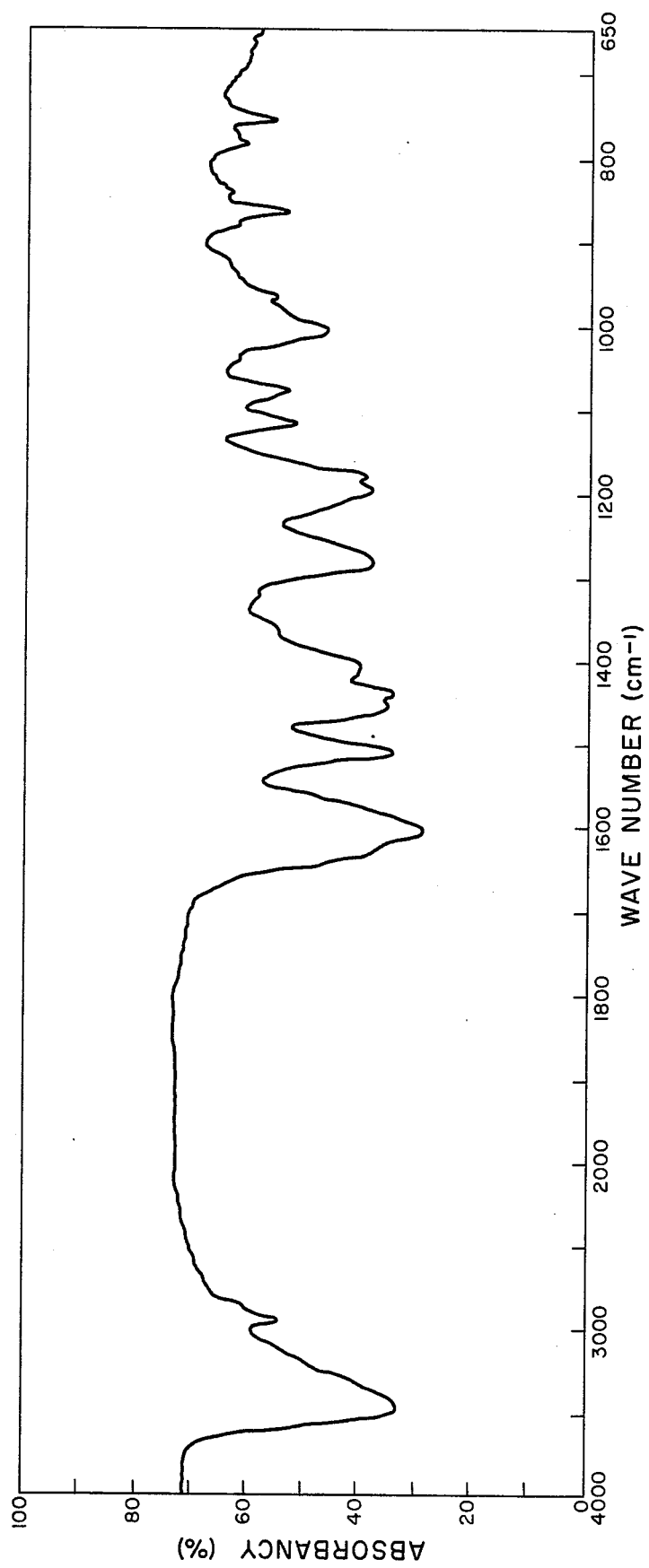
FIG. 1 shows a curve of the infrared absorption spectrum of a sample of neothramycin A pelleted in potassium bromide.
Figure 2:
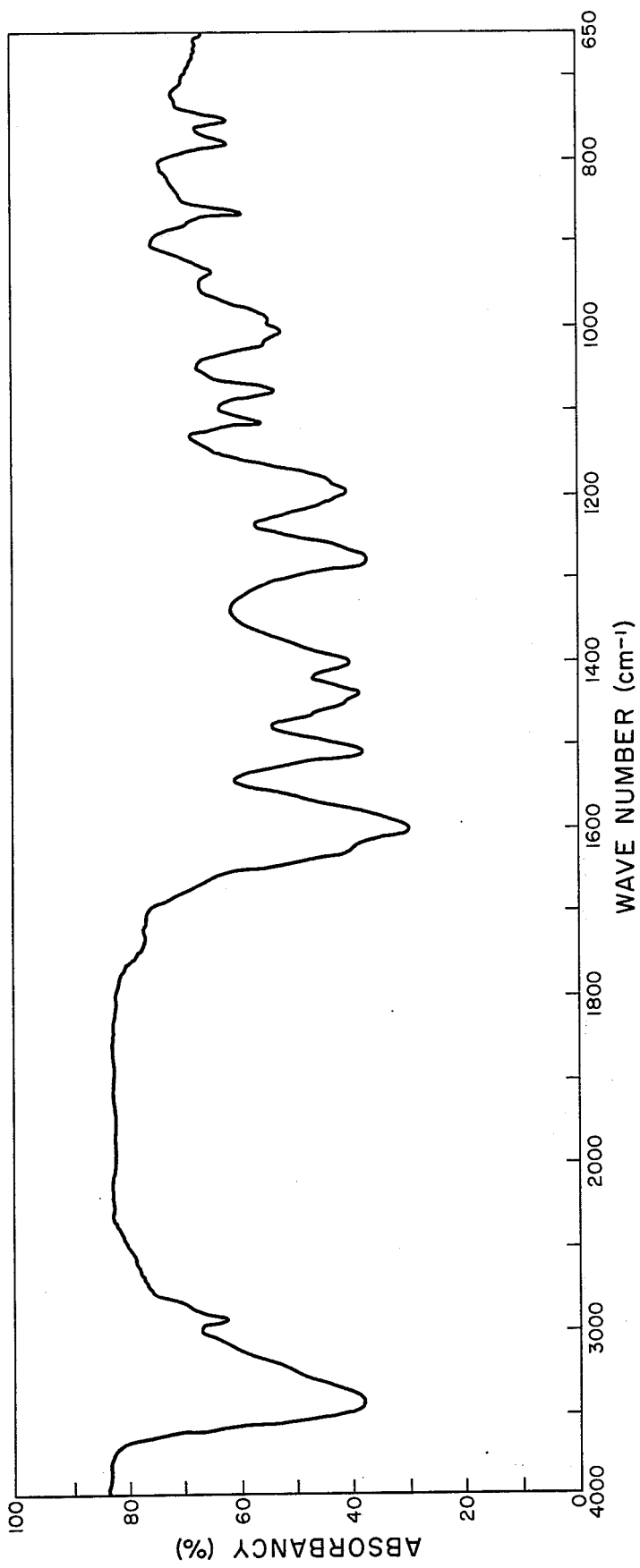
FIG. 2 shows a curve of the infrared absorption spectrum of a sample of neothramycin B pelleted in potassium bromide.
Figure 3:
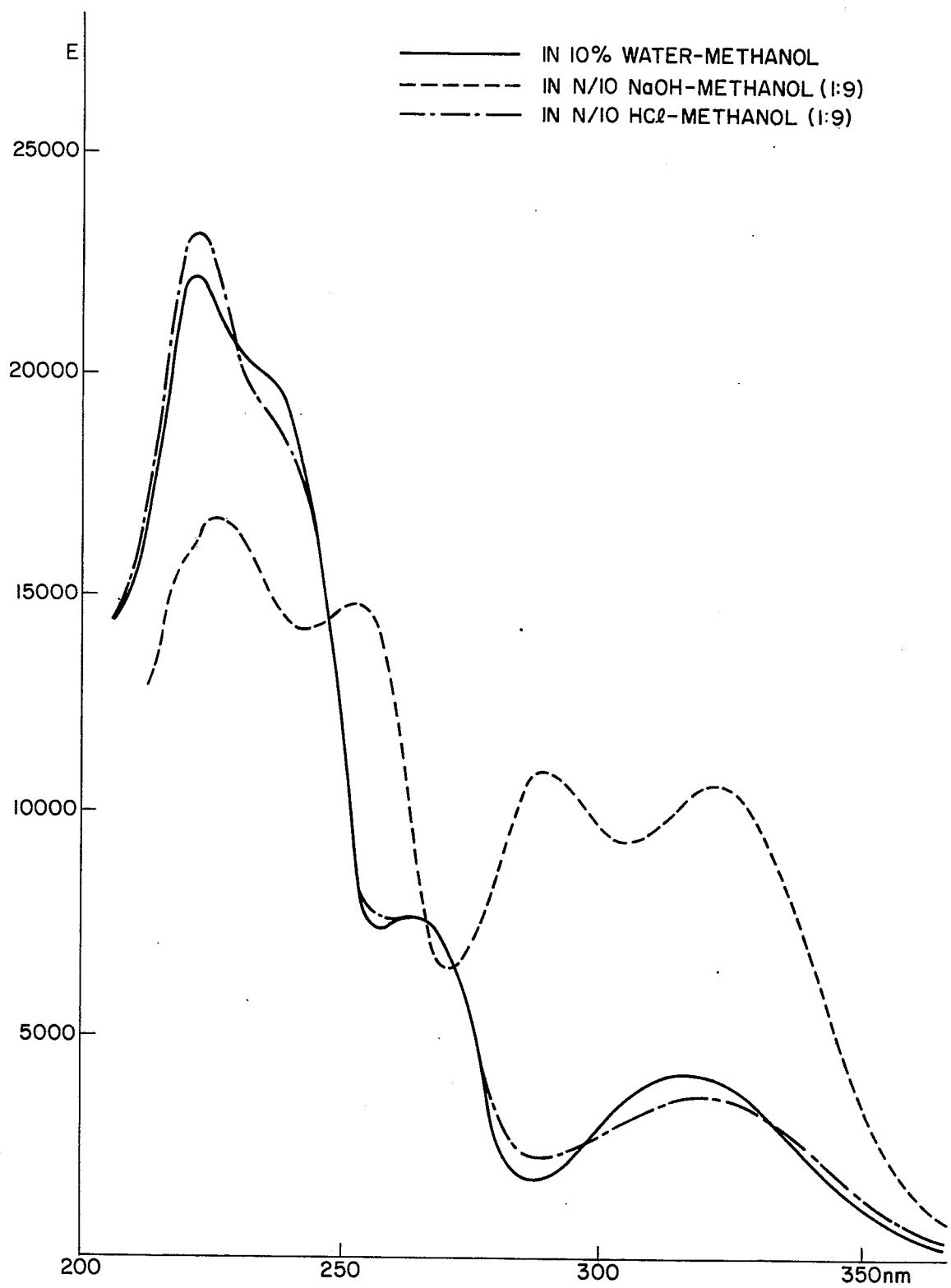
FIG. 3 shows curves of the ultraviolet absorption spectrum of a sample of neothramycin A dissolved in 10% water-methanol, in N/10 NaOH-methanol (1:9) and in N/10 HCl-methanol (1:9), respectively.
Figure 4:
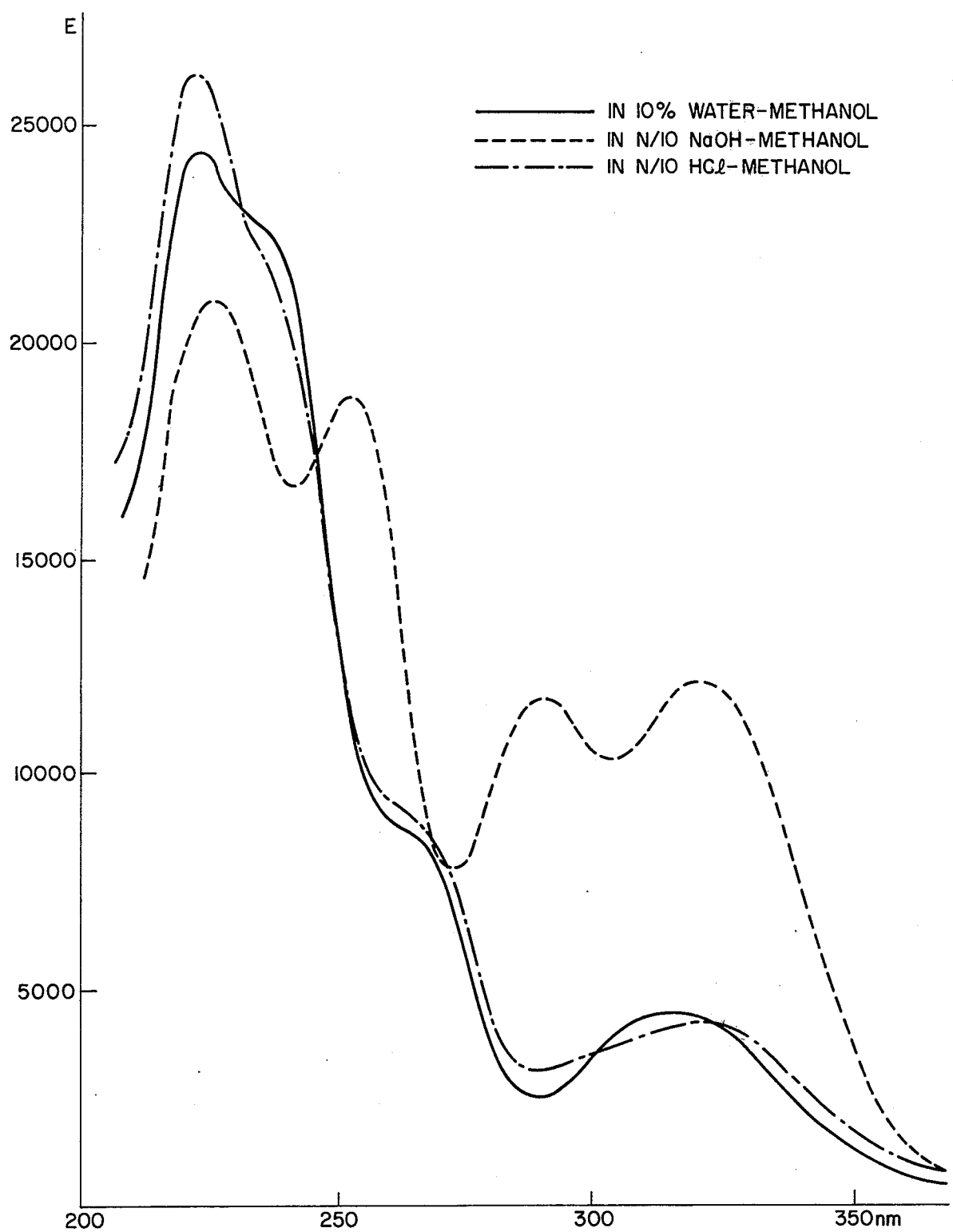
FIG. 4 shows curves of the ultraviolet absorption spectrum of a sample of neothramycin B dissolved in 10% water-methanol, in N/10 NaOH-methanol (1:9) and in N/10 HCl-methanol (1:9), respectively.

The neothramycin A and neothramycin B of this invenion have low antibacterial and antifungal activity as will be clear from the antibacterial spectra of these substances shown in Table 2 below. The minimum inhibitory concentrations (mcg./ml.) of neothramycin A and B to various bacteria have been determined on nutrient agar plates which were incubated at a temperature of 37° C. for 17 hours. The minimum inhibitory concentrations to various fungi have been determined on nutrient agar plates containing 1% glucose after incubation at 27° C for 40 hours.

Table 2

| Test organisms | Minimum Inhibitory Concentrations (Mcg./ml.) | |
|---|---|---|
| | MC916-A | MC916-B |
| *Staphylococcus aureus* Smith | 50 | 100 |
| *Staphylococcus aureus* 209P | >100 | >100 |
| *Klebsiella pneumoniae* PCI 602 | 50 | 100 |
| *Escherichia coli* NIHJ | 100 | 100 |
| *Escherichia coli* K-12 | 100 | 100 |
| *Pseudomonas aeruginosa* No. 12 | >100 | >100 |

Table 2-continued

| Test organisms | Minimum Inhibitory Concentrations (Mcg./ml.) | |
|---|---|---|
| | MC916-A | MC916-B |
| Bacillus subtilis PCI 219 | 100 | >100 |
| Escherichia coli W677 | 50 | 100 |
| Escherichia coli JR66/W677 | 100 | >100 |
| Aeromonas salmonecida ATCC 14174 | 25 | 50 |
| Vibrio anguillarum NCBM 6 | 50 | 100 |
| Saccharomyces cerevisiae | 50 | >100 |
| Candida albicans 3147 | >100 | >100 |
| Aspergillus niger | 100 | >100 |
| Piricularia oryzae | 50 | >100 |
| Xanthomonas citri | >100 | >100 |
| Xanthomonas oryzae | 50 | 100 |

As stated hereinbefore, neothramycin A and B of this invention have a high inhibitory activity to the growth of leukemia cells and are expected to be useful as an agent for treating therapeutically a living animal affected by leukemia. Chemotherapeutic effects of the neothramycin A and B against leukemia L-1210 in mice were investigated in the following manner. Luekemia L-1210 cells ($10^5$ cells/mouse) were injected intraperitoneally in mice of CDF 1 strain weighing 19–22 g. For the treatment of the leukemia so infected, administration of neothramycin A and B were commenced immediately after the tumor inoculation. The leukemic mice were used in groups each of four mice for each dose. When 300, 150, 75, 37.5 and 18.7 mcg./mouse/day of the neothramycin A and B were dosed by intraperitoneal injection once daily for 10 days, the highly favorable effects on the survival ratio (%) were observed as will be clear from the results shown in Table 3 below.

TABLE 3

| Dosage (mcg/mouse/day) | Average of Survival Rate (%) | |
|---|---|---|
| | Neothramycin A | Neothramycin B |
| 300 | death (toxic dose) | death (toxic dose) |
| 150 | 200 | 192 |
| 75 | 167 | 154 |
| 37.5 | 154 | 128 |
| 18.7 | 122 | 103 |

The survival Ratio (%) is calculated by dividing the number of days of survival of the treated animals (e.g. 10) by the number of days of survival of the control animals (e.g. 8) and multiplying by 100, e.g. 10/8 × 100 = 125. Ratios greater than 125 are generally considered significant.

An effective prolongation in the survival rate (%) of mice inoculated with leukemia L-1210 was also observed by treatment with methylneothramycin A or methylneothramycin B, as shown in Table 4 below.

TABLE 4

| Dosage (mcg/mouse/day) | Average of Survival Rate (%) | |
|---|---|---|
| | Methylneothramycin A | Methylneothramycin B |
| 200 | Toxic | Toxic |
| 100 | 128 | 154 |
| 50 | 103 | 147 |
| 25 | — | 115 |
| 12.5 | — | 103 |

The neothramycin A and B of this invention are of a low toxicity to animal and man, as shown by the fact that the neothramycin A and B exhibit $LD_{50}$ values of 20–30 mg./kg. and 20–30 mg./kg., respectively, in mice, when a solution of 0.25–0.5% by weight of neothramycin A or B in 10% dimethylsulfoxide-water is injected intraperitoneally in mice for the purpose of estimating the acute toxicity of these substances.

According to a second aspect of this invention, there is provided a process for the production of neothramycin A and neothramycin B, which comprises cultivating a neothramycin-producing strain of the genus Streptomyces under aerobic conditions in a suitable culture medium therefor containing assimilable carbon and nitrogen sources for a period of time sufficient to produce and accumulate neothramycin A and neothramycin B in the culture medium, and recovering a mixture of the neothramycin A and neothramycin B from the culture, and subsequently, if required, separating the recovered mixture into the neothramycin A and neothramycin B in their isolated forms. For the production of neothramycin according to the process of this invention, a strain of the genus Streptomyces may be used as long as this strain produces neothramycin. A suitble example of the strain which may be employed in this invention for the production of neothramycin is the above-mentioned MC916-C4 strain of Streptomyces. This MC916-C4 strain was deposited on Feb. 2, 1974 in a Japanese authorized depository "Fermentation Research Institute, Agency of Industrial Science and Technology", Inage, Chiba-City, Japan, under deposit number FERM-P 2452. This MC916-C4 strain was also deposited in the American Type Culture Collection, Washington, D. C., U.S.A. under A.T.C.C. number 31123.

Cultural and taxonomic characteristics of the MC916-C4 strain are described below.

1. Microscopical morphology

MC916-C4 strain has branched substrate mycelia from which aerial hyphae develops in the form of hook or open spirals. No whorl-branching is observed. Matured spore chains usually bear more than 10 conidal spores. Spores measure about 0.6–0.8 by 1.0–1.2 microns in size and have a smooth surface.

2. Characteristics of the growth on various culture media

The designation of colors in brackets [ ] mentioned below follows the color standard given in the "Color Harmony Manual" published by Container Corporation of America.

(1) On sucrose-nitrate agar (incubated at 27° C.): Pal yellow to reddish yellow [3 pc, amber] colored growth bears thin aerial hyphae of light brownish gray to light gray color. Soluble pigment is faintly tinged with yellow.

(2) On glucose-asparagine agar (incubated at 27° C.): Dull yellow orange [3nc, Amber to 4pe, Orange Rust] colored growth develops aerial hyphae of light gray to light brownish gray color [2ih, Dk covert Gray]. Soluble pigment is faintly tinged with yellow.

(3) On glycerol-asparagine agar (ISP No. 5 medium, incubated at 27° C.): Dark yellow orange to yellowish brown [3pi, Golden Brown] colored growth develops aerial hyphae of brownish gray [3ih, Beige Gray] to gray [5ih, Shadow Gray] color. Soluble pigment with yellowish tinge to yellowish brown tinge is produced.

(4) On inorganic salts-starch agar (ISP No. 4 medium, incubated at 27° C.): Pale yellowish brown to yellowish brown [3pi, Golden Brown] colored growth develops aerial hyphae of light brownish gray [3fe, Silver Gray] color. Soluble pigment is tinged with brown. The reverse side of the growth is dark yellowish brown in color.

(5) On tyrosine agar (ISP No. 7 medium, incubated at 27° C.): Dark yellow to yellowish brown [4pg, Dark Luggage Tan] colored growth bears aerial hyphae of light brownish gray. Soluble pigment is tinged with dark yellow to yellowish brown.

(6) On nutrient agar (incubated at 27° C.): The growth is colored pale yellowish brown to pale brown without developing aerial hyphae. Soluble pigment is faintly tinged with brown.

(7) On yeast extract-malt extract agar (ISP No. 2 medium, incubated at 27° C.): Yellowish brown [4pg., Dk Luggage Tan] to yellow orange [4pe, Orange Rust] colored growth develops aerial hyphae of light gray [2fe, Covert Gray] to light brownish gray [2ih, Dk Covert Gray] color. Soluble pigment of yellowish brown to brown color is produced. The reverse side of the growth is colored dark yellowish brown.

(8) On oatmeal agar (ISP No. 3 medium, incubated at 27° C.): Reddish yellow to dark yellow orange [4pe, Orange Rust] colored growth with aerial hyphae of light gray [5fe, Ashes] to brownish gray [3ih, Beige Gray] color. Soluble pigment is tinged with yellow.

(9) On glycerol-nitrate agar (incubated at 27° C.): Pale yellow to reddish yellow [3pc, Amber] colored growth bears slightly developed aerial hyphae of brownish white to light brownish gray color. Soluble pigment is faintly tinged with yellow.

(10) On starch agar (incubated at 27° C.): The growth is colored dull yellow to yellowish brown [2pi, Mustard Brown] without developing aerial hyphae or rarely with developing aerial hypae of white. Soluble pigment is faintly tinged with brown.

(11) On calcium-malate agar (incubated at 27° C.): The growth is colored pale yellow to pale olive without developing aerial hyphae or with slightly developing aerial hyphae of white. Soluble pigment is faintly tinged wtih yellow.

(12) On cellulose (incubated at 27° C.): Colorless growth without aerial hyphae. No soluble pigment is produced.

(13) On gelatin stab: On plain gelatin medium (incubated at 20° C.), the growth is colorless to dull yellow colored without developing aerial hyphae, and with producing soluble pigment of faintly yellow tinge. on glucose-peptone-gelatin medium (incubated at 27° C.), the growth is pale yellow to dull yellow in color. Aerial hyphae are not developed initially but ones of grayish white color are produced later. No production of soluble pigment is observed.

(14) On skimmed milk (incubated at 37° C.): The growth is colored pale yellow to pale orange without developing aerial hyphae. Soluble pigment is very faintly tinged with orange.

3. Physiological properties (1) Temperature for growth

Growth on glucose asparagine agar was examined at 20° C., 24° C., 27° C., 30° C., 37° C., and 50° C. The MC916-C4 strain grew at all temperatures tested, except at 50° C. Optimum temperature for good growth was observed to be in the vicinity of 30° C.

(2) Liquefaction of gelatin

Plain gelatin (15%) medium started to liquefy from the fifth day of incubation at 20° C. The degree of liquefaction was medium. The gelatin (15%) in glucosepeptone-gelatin medium started to liquefy from the second day of incubation when incubated at 27° C., and the grade of liquefaction was then medium to strong.

(3) Hydrolysis of starch

Starch in inorganic salts-starch-agar medium and in starch-agar medium was hydrolyzed starting from the fifth day of incubation when incubated at 27° C. The grade of hydrolysis was medium to strong.

(4) Coagulation and peptonization of skimmed milk

When incubated at 37° C., the coagulation of skimmed milk started at the fourth day of incubation and the peptonization was observed at the fifth day of incubation after the coagulation was complete. The grades of coagulation and peptonization were medium to strong.

(5) Formation of melanoid pigment

No pigmentation was observed neither on tryptonyeast extract broth (ISP No. 1 medium), nor on peptoneyeast extract iron agar (ISP No. 6 medium), nor on tyrosine agar (ISP No. 7 medium), when incubated at 27° C.

(6) Utilization of carbon sources for growth

Utilization of the following carbohydrates was tested in Pridham-Gottlieb agar medium (ISP No. 9 medium ) as incubated at 27° C.

Glucose and L-rhamnose were utilized for growth. L-Arabinose, D-fructose, sucrose, inositol and D-mannitol were not utilized. Utilization of D-xylose was doubtful. Raffinose was sometimes utilized but not utilized other times.

(7) Liquefaction of calcium malate

Calcium malate in calcium malate-agar medium was liquefied around the growth starting at the 9th days of incubation, when incubated at 27° C. The grade of liquefaction was medium to strong.

(8) Reduction of nitrate

Reduction of nitrate was observed in aqueous peptone solution containing 1.0% sodium nitrate (ISP No. 8 medium), when incubated at 27° C.

Summarizing the above-mentioned characteristics of the MC916-C4 strain, it is noted that this strain belongs to the genus Streptomyces and that the aerial hyphae form open spirals but does not develop whorl. The surface of spore is smooth under microscopic observation. On various media, the growth has a color of yellowish orange to yellowish brown with developing aerial hyphae of light brownish gray to brownish gray color. Soluble pigment is tinged with yellow to brown or with yellowish brown. No melanoid pigment is produced. Proteolysis and starch hydrolysis are of medium to strong grade.

On the basis of the above-mentioned properties, the MC916-C4 strain is compared to known analogous species of Streptomyces with reference to descriptions of International Streptomyces Project (ISP). It is found that the MC916-C4 strain resembles *Streptomyces naraensis* (see "International Journal of Systematic Bacteriology" Vol. 22, page 323 (1972). However, it is noted that the MC916-C4 strain is different from *Streptomyces naraensis* ISP 5508 strain in respect to their utilization of carbon sources. *S. naraensis* produces cycloheximide, similarly to the MC916-C4 strain. Furthermore, among cycloheximide-producing strains, it is found that strains of Group C which are analogous to *Streptomyces griseolus* as reported in an article by T. Furumai et al. titled "On cycloheximide-producing microorganisms" [see the "Journal of Antibiotics" Ser. B., Vol. 17, No. 4, page 181 (1964)] are very similar to the MC916-C4 strain.

The MC916-C4 strain is well coincident with the above Group C strains in many respects, though the MC916-C4 strain has not been tested as to whether it has the properties of hemolysis, liquefaction of serum and utilization of galactose and lactose which were shown by the Group C strains. However, those Group C strains are not available at present, as they are already dead. In this situation, comparison of the MC916-C4 strain is now made with *Streptomyces sp.* IFO 3300 which is known to produce fermicidin, an antibiotic analogous to cycloheximide, and which is reported in the above article by T. Furumai et al. to be well coincident with said Group C strains. The results of comparison are shown in Table 5 below, with reference to the descriptions of the "Journal of Antibiotics".

strain with *Streptomyces sp.* IFO 3300, *Streptomyces griseolus* ISP 5067 and *Streptomyces naraensis* ISP 5508 are carried out. It has been found that the MC916-C4 strain is related to *Streptomyces sp.* IFO 3300 and *Streptomyces naraensis* ISP 5508 and most to the former strain. The IFO 3300 strain is somewhat different from the MC916-C4 strain having a tinge of orange in the color of growth. The MC916-C4 strain is clearly distinguished from said ISP 5508 strain in respect to the reduction of nitrate and from said ISP 5067 strain in respect to the formation of spirals, utilization of carbon sources and reduction of nitrate.

Mutation of actinomycetes occurs frequently in either artificial or spontaneous conditions. Accordingly, this invention includes the use of the MC916-C4 strain as Table 5

| Properties | MC916-C4 strain | *Streptomyces* sp. IFO 3300 (analogous to *Streptomyces griseolus*) | Descriptions of *Streptomyces* sp. IFO 3300 shown in literature* | Descriptions of Group C strains shown in literature* |
|---|---|---|---|---|
| Formation of spirals | + | ± | (+) | + |
| Spore surface | Smooth | | Smooth** | Smooth |
| Color of aerial hyphae | Light brownish gray to brownish gray | Light brownish gray to brownish gray | Gray | Brownish gray |
| Color of growth | Yellow orange to yellowish brown | Colorless to pale yellowish brown | Creamy to brown tinge | |
| Soluble pigment | Yellow to brown tinge to yellowish brown | Not observed or with brown tinge | Not observed or with brown | |
| Formation of melanin-like pigment | | | | |
| On ISP No. 1 medium | − | − | −** | − |
| On ISP No. 6 medium | − | − | −** | − |
| On ISP No. 7 medium | − | − | −** | − |
| Hydrolysis of starch | + | + | + | + |
| Coagulation of milk | + | + | − | + |
| Peptonization of milk | + | + | − | + |
| Liquefaction of gelatin in plain gelatin medium | + | + | Slightly liquefied | + |
| in glucose-peptone-gelatin medium | + | + | ± | |
| Reduction of nitrate | + | + | + | Sometimes + but other times − |
| Utilization of carbon sources | | | | |
| Glucose | + | + | | |
| L-Arabinose | − | − | | |
| D-xylose | ± | ± | | Sometimes + but other times − |
| D-Fructose | − | ± | | |
| Sucrose | − | − | | |
| Inositol | − | − | | |
| L-Rhamnose | (+) | + | | |
| Raffinose | ± | ± | | |
| D-Mannitol | − | − | | |
| Antibiotics produced | Cycloheximide & neothramycin A and B | | Fermicidin (antiobiotic analogous to cycloheximide) | Cycloheximide |

Notes:
Literature* denotes the "Journal of Antibiotics" Ser. B. Vol. 7, No. 7, page 221 (1954).
Literature** denotes the "Journal of Antibiotics" Ser. B. Vol. 17, No. 4, page 181 (1964).
In respect to the utilization of carbon sources: the symbol ± means probably no utiization.
The symbol (+) means probable utilization.

As will be seen from the above Table, the MC916-C4 strain is coincident with the Group C strain described inthe above-metnioned literature but is differentiated from *Streptomyces sp.* IFO 3300 strain in respect to th coagulation and peptonization of milk.

Furthermore, the MC916-C4 strain is different from *Streptomyces griseolus* [see the "International Journal of Systematic Bacteriology" Vol. 18, page 122 (1968)] which has been reported to resemble said IFO 3300 strain, in that *S. griseolus* does not form open spirals in the aerial hyphae thereof and is somewhat different from the MC916-C4 strain in respect to the utilization of carbon sources. Further comparisons of the MC916-C4 well as it mutants. In other words, this invention includes the use of all strains of the genus Streptomyces which produce neothramycin.

Neothramycin can be obtained by aerobic cultivation of spores or mycelia of a neothramycin-producing strain of the genus Streptomyces such as *Streptomyces sp.* MC916-C4 strain (identified as A.T.C.C. 31123). In carrying out the process of the second aspect of this invention, an amount of spores or mycelia of a neothramycin-producing strain is inoculated to a suitable culture medium therefor comprising nutrient sources and is then incubated under aerobic conditions so that there is obtained a culture broth containing neothramycin. Generally, constituents of culture media commonly employed for the cultivation of ordinary actinomycetes can be used for the purpose of this invention. For instance, commercially available soybean meal, peanut powder, cotten speed powder, dried yeast, peptone, meat extract, casein, corn steep liquor, N-Z amine, ammonium nitrate, ammonium sulfate and the like may be useful as the nitrogen sources. Commercially available carbohydrates such as glucose, starch, glycerol, maltose, dextrin, saccharose, lactose, molasses and the like as well as fat or oil are useful as the carbon source. In addition, sodium chloride, calcium carbonate, magnesium sulfate, manganese chloride, sodium phosphate or other inorganic salts can be employed for the salt-additive in the culture medium. Various heavy metal salts may also be added in trace quantities, if required. Any of the nutrient materials which are known for the cultivation of actinomycetes may be employed in the process of this invention, as long as it is assimilable by the neothramycin-producing strain for the production of neothramycin.

For the production of neothramycin on a large scale, liquid cultivation is preferred. Any temperature at which the neothramycin-producing strain is able to grow and produce the neothramycin can be employed for the cultivation, but a preferred cultivation temperature is within a range of 25° to 35° C. The cultivation is continued for a period of time sufficient to produce and accumulate a sufficient amount of the neothramycin A and B in the culture medium. For instance, a culture medium comprising 2% glucose, 2% glycerol, 1.2% soybean meal, 1.0% cotton seed flour, 0.32% calcium carbonate, 0.5% sodium chloride and 0.0005% manganese chloride tetrahydrate was prepared and sterilized at pH 6.8. This medium was then inoculated with spores or mycelia harvested from a slant culture of the MC916-C4 strain. When it was shake-cultivated aerobically at 28° C., the production and accumulation of neothramycin in the culture medium reached a maximum at the end of incubation for 3 to 5 days.

Assay of neothramycin can be made using *Staphylococcus aureus* or *Escherichia coli* as the test organism according to a standard cup-plate method which has usually been employed for the assay of known antibiotics. A pure neothramycin A which was obtained from the Example 3, described later, of this invention may be used as an authentic sample which exhibits a potency of 1000 units per mg. In case the other antibiotic substances such as cycloheximide are simultaneously produced in the culture broth of the MC916-C4 strain in addition to the neothramycin, the culture broth may be washed with ethyl acetate or other suitable organic solvent to remove such other antibiotic substances by extraction. The remaining aqueous phase may then be employed for the assay of the contents of the neothramycin A and B according to the aforesaid standard cup-plate method.

For the recovery of the neothramycin from the culture medium, the culture broth of the neothramycin-producing strain may either be treated with a suitable organic solvent such as n-butanol to provide an extract of the neothramycin in said solvent or may be treated with a suitable adsorbent such as active carbon to make the neothramycin adsorbed by the adsorbent. Distribution of the neothramycin A or neothramycin B between n-butanol and water was examined, and it is found that the partition coefficient of the neothramycin in n-butanol/water is greater than 5 at a pH value of 2 to 7. Accordingly, the neothramycin can be extracted with n-butanol from the aqueous culture broth which has been adjusted to a pH value of 2 to 7 and preferably of about 6. The neothramycin is substantially insoluble in and hence is practically not extractable with ethyl acetate or chloroform from the liquid portion of the culture broth. If required, therefore, it is possible to treat the culture broth with ethyl acetate or chloroform for extraction in order to remove the soluble impurities from the culture broth. To separate the neothramycin from the culture broth it is preferred that the culture broth is treated with active carbon as the adsorbent. The neothramycin which has been adsorbed by active carbon can be eluted therefrom by means of a mixture of methanol and water, a mixture of propanol and water or a mixture of acetone and water, etc. The efficiency of the elution may be improved when the elution is done under weakly alkaline conditions. Purification of the neothramycin can be made using the abovementioned extraction method and adsorption-elution method in a suitable combination of them or in a repeated manner. Further purification may be achieved by a usual column chromatography on Sephadex LH-20 (a commercial product sold by Pharmacia Co., Sweden) or silica gel. The known antibiotic cycloheximide which may frequently be co-existent in the culture broth of the MC916-C4 strain can readily be separated from the neothramycin of this invention by extracting with ethyl acetate or by chromatography on Sephadex LH-20.

To isolate the neothramycin A from the neothramycin B, a mixture of the neothramycin A and neothramycin B may be subjected to a column chromatography on silica gel with chloroform-methanol (30:1 volume) as the developing solvent. The isolated neothramycin A or the isolated neothramycin B can be purified by column chromatography on silica gel using suitable mixed organic solvents as the developing solvent.

The recovery of the neothramycin A and neothramycin B may typically be carried out in the following way: The culture broth containing the neothramycin is at first filtered or centrifuged to remove the solid matters together with the mycelia. The broth filtrate is then treated with active carbon to adsorb the neothramycin therefrom. The active carbon carrying the adsorbed neothramycin is eluted with 50% acetone-water (a mixture of acetone and water at a ratio of 1:1 by volume) at pH 8.0. The eluate is collected in fractions and the active fractions are combined together and concentrated to dryness under reduced pressure at a temperature of up to 40° C. or otherwise freeze-dried to give a crude powder. This crude powder is extracted with aqueous ethanol so that a greater part of the active components is separated in the resulting extract. This extract is concentrated to dryness under reduced pressure at a temperature of up to 40° C. or otherwise freeze-dried to give a second crude powder. A solution of this crude powder in methanol is passed through a column of Sephadex LH-20 (a product of Pharmacia Co., Sweden) which is subsequently developed with methanol. During this chromatographic process, the possibly co-existing cycloheximide is eluted in such fractions running out in the first-half phase of the process, whereas the mixture of the neothramycin A and B is eluted in such fractions running out in the later-half phase of the process.

The active fractions containing the neothramycin A and B are combined together and then concentrated to dryness under reduced pressure at a temperature of up to 40° C., to afford a crude powder. This powder is taken into a small volume of methanol and the methanolic solution is uniformly admixed with an amount of neutral silica gel. The admixture was dried by evaporation and then placed on the top of a column of a further amount of said neutral silica gel which has been impregnated with a mixture of chloroform and ethanol (30:1 by volume). The silica gel column is subsequently developed with the chloroform-ethanol (30:1 by volume). During this chromatography process, the neothramycin A is eluted in the active fractions running in the first-half phase of the process, while the neothramycin B is eluted in the active fractions running out in the later-half phase of the process. The active fractions containing the neothramycin A and the active fractions containing the neothramycin B are concentrated to dryness under reduced pressure at a temperature of up to 40° C., respectively, to give a crude powder of the neothramycin A and a crude powder of the neothramycin B.

The crude powder of the neothramycin A so obtained is taken into an appropriate amount of chloroform and the solution is passed through a column of a neutral silica gel which has been impregnated with chloroform. This silica gel column is washed with chloroform and then developed at 5° C. with chloroform-ethanol (60:1 by volume). The eluate is collected in fractions, and the desired active fractions solely containing the neothramycin A are detected by referring to test results of biological assay and thin layer chromatography of each fraction. The desired active fractions so chosen are combined together and concentrated to dryness under reduced pressure at a temperature of up to 40° C. to give the neothramycin A as a colorless powder. This powder may further be purified to a colorless powder of a pure neothramycin A by repeating the above-mentioned silica gel chromatographic process or by dissolving said powder into a small volume of chloroform, adding ethyl ether to the chloroform solution, filtering off and drying the resulting precipitate. A colorless powder of pure neothramycin B may be obtained from the aforesaid crude powder of the neothramycin B by purifying in the same manner as for the neothramycin A. It is preferred, however, that the column chromatography on silica gel is made using a mixture of chloroform and ethanol (100:1 by volume) as the developing solvent.

In view of the aforesaid properties of the neothramycin A and neothramycin B, it has been confirmed that these substances are new antibiotics which are differentiated from any of the known antibiotics. According to a third aspect of this invention, there is provided a method for therapeutically treating a living animal, including man, affected by leukemia, which comprises adminstering the neothramycin A and/or the neothramycin B to said animal in a dosage sufficient to reduce the affection by leukemia. According to a fourth aspect of this invention, there is further provided a pharmaceutical composition comprising the neothramycin A and/or the neothramycin B in an amount sufficient to reduce the affection by leukemia in vivo, the neothramycin A and/or the neothramycin B being in combination with a pharmaceutically acceptable carrier. It will be appreciated that the actual preferred amounts of the neothramycin used will vary according to the particular compound being used, the particular composition formulated, the mode of application and the particular situs and organism being treated. Many factors that modify the action of the drug will be taken into account by the skilled in the art, for example, age, body weight, sex, diet, time of administration, route of administration, rate of excretion, drug combinations, reaction sensitivities and severity of the disease. Optimal application rates for a given set of conditions can be ascertained by the skilled in the art using conventional dosage determination tests in view of the above guidelines.

It is believed that using the preceding description and without further elaboration, one skilled in the art can utilize the concept of this invention to its fullest extent. The following preferred specific embodiments are, therefore, to be construed as merely illustrative and not limitative of the remainder of the disclosure in any day.

DESCRIPTION OF THE PREFERRED EMBODIMENTS

EXAMPLE 1

A loopful quantity of *Streptomyces sp.* MC916-C4 (identified as A.T.C.C. 31123) which was incubated in slant agar medium was inoculated to a sterile liquid culture medium (pH 7.0, 125 ml.) comprising 2.5% maltose, 0.75% peptone, 0.75% meat extract, 0.3% yeast extract, 0.2% sodium chloride and 0.1% magnesium sulfate ($7H_2O$). The inoculated medium was shake-cultured at 28° C. for 48 hours to give a primary seed culture. This primary seed culture was inoculated at an inoculum size of 0.48% by volume to 50l of a sterilized liquid culture medium (pH 7.0) containing 3.5% starch syrup, 0.75% peptone, 0.75% meat extract, 0.3% yeast extract, 0.3% sodium chloride and 0.1% magnesium sulfate ($7H_2O$) in a stainless steel fermentor of a capacity of 130l. The inoculated medium was cultured at 28° C. for 24 hours under aeration and agitation to provide a secondary seed culture. This secondary seed culture was inoculated at an inoculum size of 2% by volume (6l) to a liquid culture medium (pH 6.8, 300l) comprising 2% glucose, 2% glycerol, 1.2% soybean meal, 1.0% cotton seed powder, 0.32% calcium carbonate, 0.5% sodium chloride and 0.0005% manganese chloride ($4H_2O$) which had been sterilized at 120° C. for 30 minutes. The cultivation was made at 28° C. for 92 hours under aeration and agitation (250 r.p.m.) while the rate of aeration was 150 l/minute for the first 24 hours and then increased to 300 l/minute for the subsequent period of 24th hour to 92 hour of the cultivation.

The resulting culture broth (pH 7.3, 300l, potency 88 u./ml.) was admixed with 24 kg. of a filter aid (diatomaceous earth commercially available under a trade name "Hyflo-supercel") and the admixture was filtered by means of a press-filter to give 300l of the broth filtrate. The broth filtrate was well admixed with 3 Kg. of active carbon at ambient temperature for 1 hour under agitation, so that the antibiotics were adsorbed on the carbon.

The active carbon portion was collected by centrifugation and then washed with 150l of water. The washed carbon was admixed with 70 l of 50% acetone-water (pH 8.0) for 1 hour under agitation, so that the antibiotics were extracted into the solvent. This extraction was conducted twice and the extracts so obtained were combined together to a volume of 118l. The extract solution was concentrated under reduced pressure at a temperature of up to 40° C. and the concentrated solution (2.6l) was freeze-dried to give 565 g. of a brown colored powder (potency, 35 u./mg.) which contained the neothramycin A and B. This brown colored powder was extracted with 11.6l of 80% ethanol-water. The insoluble matters which had no antibacterial activity were removed by filtration, to yield 11.2 l of an ethanolic extract. This extract was concentrated under reduced pressure at a temperature of up to 40° C. to a volume of 800 ml., and the concentrated solution was freeze-dried to afford 218.5 g. of a crude powder (potency, 53 u./mg.). This crude powder was divided into five equal parts, and each part was dissolved in 20 ml. of methanol. The methanolic solution was passed through a column (90 mm diameter) of 4 l of Sephadex LH-20, which was subsequently developed with methanol. The eluate was collected in 200 ml. fractions, and it was found that cycloheximide was eluted out in the fraction Nos. 9 to 11 while a mixture of the MC916-A and -B substances was eluted in the fraction Nos. 12 to 14. The fraction Nos. 12-14 were combined together and concentrated to dryness under reduced pressure at a temperature of up to 40° C. to give 47 g. of a crude powder (potency, 160 u./mg.) comprising the mixed neothramycin A and B. Yield 28% (based on the neothramycin content of the broth).

EXAMPLE 2

The crude powder (33 g.) comprising the mixed neothramycin A and B obtained in Example 1 was taken into a small volume of methanol, and the solution was uniformly mixed wih 60 g. of a neutral silica gel, followed by drying under reduced pressure. The dried mass so obtained was placed on the top of a column (60 mm diameter) of 660 g. of said neutral silica gel which had been impregnated with chloroform-ethanol (30:1 by volume). This silica gel column was developed at 5° C. by passing a flow of chloroform-ethanol (30:1 by volume) through said column. The eluate was collected in 130 ml. fractions, and it was found that the neothramycin A was eluted in the fraction Nos. 23-31 while the neothramycin B was eluted in the fraction Nos. 35-49. The combined active fraction Nos. 23-31 was concentrated to dryness under reduced pressure at a temperature of up to 40° C. to give 1.47 g. of a yellowish crude powder of the neothramycin A (potency, 520 u./mg.). Yield 14%. The combined fraction Nos. 35-49 were concentrated to dryness in the same manner to give 1.03 g. of a yellowish crude powder of the neothramycin B (potency, 450 u./mg.). Yield 9%.

EXAMPLE 3

The yellowish crude powder of the neothramycin A (1 g.) obtained in Example 2 was dissolved in 20 ml. of chloroform, and the solution was passed at 5° C. through a column (13 mm diameter) of 20 g. of a neutral silica gel of the same grade as employed in Example 2 which had been impregnated with chloroform. The column was washed with 400 ml. of chloroform and subsequently developed with chloroform-ethanol (60:1 by volume). The eluate was collected in 8 ml. fractions, and it was found that the neothramycin A was eluted in the fraction Nos. 13-27. The combined fraction Nos. 13-27 was concentrated to dryness under reduced pressure at a temperature of up to 40° C., giving 320 mg. of a faintly yellow colored powder. This powder was taken into a minimum volume of chloroform and to this solution was added ethyl ether until the precipitate formed was not longer deposited. The precipitate was removed by filtration and dried, affording 183 mg. of a colorless powder of neothramycin A (potency 1000 u./mg.). Yield 35%.

EXAMPLE 4

The yellowish crude powder of the neothramycin B (810 mg.) obtained in Example 2 was taken into 16 ml. of chloroform and the solution was passed at 5° C. through a column (13 diameter) of 16 g. of neutral silica gel of the same grade as employed in Example 2 which had been impregnated with chloroform. The column was washed with 320 ml. of chloroform and then developed with chloroform-ethanol (100:1 by volume). The eluate was collected in 6.4 ml. fractions, and it was found that the neothramycin B was eluted in the fraction Nos. 34-70. The combined fraction Nos. 34-70 was concentrated to dryness under reduced pressure at a temperature of up to 40° C. to give 160 mg. of a faintly yellow colored powder. This powder was taken into a minimum volume of cholorform, and to this solution was added ethyl ether until the precipitate was no longer deposited. The pecipitate was removed by filtration and dried, affording 85 mg. of a colorless powder of neothramycin B (potency, 620 u./mg.). Yield 14.6%.

EXAMPLE 5

The colorless powder of neothramycin A (153 mg.) obtained in Example 3 was dissolved in a small volume of ethanol and rechromatographed on a column of a neutral silica gel (4.07 g.) of the same grade as employed in Example 2 which was developed with water-saturated ethyl acetate at 5° C. The eluate was collected in 0.6 ml. fractions. The fractions (Nos. 55-95) containing neothramycin A were combined and concentrated to dryness under reduced pressure at a temperature of up to 40° C., affording 53 mg. of a colorless powder of pure neothramycin A (potency 1000 u./mg.). Yield 35%.

EXAMPLE 6

The colorless powder of neothramycin B (74 mg.) obtained in Example 4 was rechromatographed on a neutral silica gel (2.53 g.) which was developed with water-saturated ethyl acetate by the same manner as employed in Example 5. Th eluate was collected in 0.35 ml. fractions. The fractions (Nos. 75-157) containing neothramycin B were combined and concentrated to dryness under reduced pressure at a temperature of up to 40° C., affording 36 mg. of a colorless powder of pure neothramycin B (potency 835 u./mg.). Yield 65%.

EXAMPLE 7

A primary seed culture (each 0.5 ml.) of *Streptomyces sp.* MC916-C4, which was obtained by the similar manner as employed in Example 1 was inoculated to each 30 ml. of a sterilized liquid cultue medium (pH 6.8) containing 2% glucose, 2% glycerol, 1.2% soybean meal, 1.0% cottonseed powder, 0.32% calcium carbonate, 0.5% sodium chloride and 0.0005% manganese chloride (4H$_2$O) in four Erlenmeyer flasks. The inoculated medium was cultured at 28° C. for 92 hours on a rotary-shaker (220 r.p.m.). The resulting culture broth (pH 6.5, 90 ml., potency 780 u./ml.) was extracted with 90 ml. of butanol under ice-cooling. The butanol-extract was concentrated to dryness under reduced pressure at a temperature of up to 40° C., affording 242 mg. of a brownish syrup containing neothramycins A and B (potency 100 u./mg.). Yield 44%.

EXAMPLE 8

A yellowish crude powder (1.0 g., potency 765 u./mg.) containing neothramycins A and B, which was obtained by the similar was as described in Examples 1 and 2 was dissolved in 20 ml. of methanol. The methanol solution was kept at 25° C. for 16 hours and concentrated to dryness under reduced pressure, affording 1.0 g. of a mixture of methylneothramycins A and B. The mixture was chromatographed on a column of silica gel (50 g., Wako-gel C-200, Wako Chemicals, Osaka) which was developed with a mixture of benzene and methanol (20:1 in volume). The eluate was cut into 12.5 ml. fractions. Fractions (Nos. 19–25) containing methylneothramycin A and fractions (Nos. 26–38) containing a mixture of methylneothramycins A and B were obtained. The fractions Nos. 26–38 were concentrated to dryness and the residue was rechromatographed on a column of silica gel (18 g.) by the same manner described above. Fractions containing methylneothramycin A and the above-mentioned fractions containing neothramycin A were combined and concentrated to dryness yielding a colorless powder (299 mg.). The powder was crystallized with a mixture of acetone and benzene to yield 240 mg. of colorless crystals of methylneothramycin A. Fractions containing methylneothramycin B were combined and concentrated to dryness, affording 175 mg. of a colorless powder of pure methylneothramycin B.

EXAMPLE 9

Crystalline methylneothramycin A (225 mg.) obtained in Example 8 was dissolved in 45 ml. of 0.01 NCHl-dioxane (1:1 in volume) and the solution was kept at room temperature (22° C.) for 1 hour. The solution was adjusted to pH 6.0 with 1 N NaOH and concentrated to dryness under reduced pressure, affording 216 mg. of a colorless powder containing neothramycins A and B. The powder was chromatographed on a column of silica gel (20 g.) by the similar manner as employed in Example 2. Pure neothramycin A (87 mg.) and neothramycin B (69 mg) were obtained.

Hydrolysis of methylneothramycin B (100 mg.) in 20 ml. of 0.01 NHCl-dioxane (1:1 volume) at room temperature for one hour by the same way as described above gave 95 mg. of a colorless powder containing neothramycins A and B.

The Sephadex LH-20 used in the preceding examples can be replaced by other similar gel-filtration agents, e.g. Sephadex G25 to G200, Sepharose 4B and 6B (Pharmacia Fine Chemicals AB, Uppsala, Sweden) and Bio-Gel A1.5m (Bio Rad Co.). Preferred gel-filtration agents include the carboxymethyl substituted cross-linked dextran gels described in columns 3 to 4 of U.S. patent 3,819,836.

The pharmaceutically acceptable salts of the substances of the present invention include nontoxic metallic salts such as sodium, potassium, calcium and aluminum, the ammonium salt and substituted ammonium salts, e.g. salts of such nontoxic amines as trialkylamines including triethylamine, procaine, dibenzylamine, N-benzyl-beta-phenethylamine, 1-ephenamine, N,N'-dibenzylethylenediamine, dehydroabietylamine, N,N'-bis-dehydroabiethylethylenediamine, N-(lower)-alkyl-piperidine, e.g. N-ethylpiperidine, and other amines which have been used to form salts with benzyl-penicillin.

We claim:

1. The process for producing the antibiotic neothramycin complex which comprises culturing a neothramycin-producing strain of Streptomyces having the identifying characteristics of A.T.C.C. 31123 under submerged aerobic conditions in a nutrient medium containing a carbon source and a nitrogenous nutrient until a substantial amount of neothramycin is produced by said organism in said nutrient medium.

2. The process of claim 1 in which the strain of Streptomyces is cultured in a nutrient medium at a temperature in the range of 24° C. to 35° C.

3. The process of claim 1 in which the strain of Streptomyces is cultured in a nutrient medium at a temperature in the range of 25° C. to 29° C. with the pH from 6 to 8.

4. The process of claim 1 which includes the further step of recovering the neothramycin complex form the culture medium.

5. The process of claim 4 in which the neothramycin produced in the cultured broth is extracted and purified by a process which includes at least one process selected from the group consisting of salting-out, solvent precipitation, butanol extraction, dialysis, ultrafiltration, isoelectric precipitation, gel filtration, electrophoresis, electrofocusing and adsorption followed by elution from an ion exchange resin.

6. The process of claim 1 in which the solution containing neothramycin is stored in a cold or frozen state.

7. The process of claim 1 in which the solution containing neothramycin is freeze-dried.

8. The process for producing neothramycin A which comprises culturing a neothramycin A producing strain of Streptomyces having the identifying characteristics of A.T.C.C. 31123 under submerged aerobic conditions in a nutrient medium containing a carbon source and a nitrogenous nutrient until a substantial amount of neothramycin A is produced by said organism in said nutrient medium.

9. The process of claim 8 in which the strain of Streptomyces is cultured in a nutrient medium at a temperature in the range of 24° C. to 35° C.

10. The process of claim 8 in which the strain of Streptomyces is cultured in a nutrient medium at a temperature in the range of 25° C. to 29° C. with the pH from 6 to 8.

11. The process of claim 8 which includes the further step of recovering the neothramycin A from the culture medium.

12. The process of claim 11 in which the neothramycin A produced in the cultured broth is extracted and purified by a process which includes at least one process selected from the group consisting of salting-out, solvent precipitation, butanol extraction, dialysis, ultra-filtration, isoelectric precipitation, gel filtration, electrophoresis, electrofocusing and adsorption followed by elution from an ion exchange resin.

13. The process of claim 8 in which the solution containing neothramycin A is stored in a cold or frozen state.

14. The process of claim 8 in which the solution containing neothramycin A is freeze-dried.

15. The process for producing neothramycin B which comprises culturing a neothramycin B-producing strain of Streptomyces having the identifying characteristics of A.T.C.C. 31123 under submerged aerobic conditions in a nutrient medium containing a carbon source and a nitrogenous nutrient until a substantial amount of neothramycin B produced by said organism in said nutrient medium.

16. The process of claim 15 in which the strain of Streptomyces is cultured in a nutrient medium at a temperature in the range of 24° C. to 35° C.

17. The process of claim 25 in which the strain of Streptomyces is cultured in a nutrient medium at a temperature in the range of 25° C. to 29° C. with the pH from 6 to 8.

18. The process of claim 15 which includes the further step of recovering the neothramycin B from the culture medium.

19. The process of claim 18 in which the neothramycin B produced in the cultured broth is extracted and purified by a process which includes at least one process selected from the group consisting of salting-out, solvent precipitation, butanol extraction, dialysis, ultra-filtration, isoelectric precipitation, gel filtration, electrophoresis, electrofocusing and adsorption followed by elution from an ion exchange resin.

20. The process of claim 15 in which the solution containing neothramycin B is stored in a cold or frozen state.

21. The process of claim 15 in which the solution containing neothramycin B is freeze-dried.

* * * * *

UNITED STATES PATENT AND TRADEMARK OFFICE
CERTIFICATE OF CORRECTION

PATENT NO. : 4,049,497
DATED : September 20, 1977
INVENTOR(S) : Hamao UMEZAWA, Tomio TAKEUCHI, Masa HAMADA,
Shinichi KONDO, Masaaki ISHIZUKA, Hiroshi NAGANAWA It is certified that error appears in the above-identified patent and that said Letters Patent are hereby corrected as shown below:

In the first column of the front page following "[30] Foreign Application Priority Data" after "Mar. 12, 1974 Japan...." delete "49-2767" and insert therefor --- 49-27674 ---.

Signed and Sealed this

Thirteenth Day of June 1978

[SEAL]

Attest:

RUTH C. MASON
Attesting Officer

DONALD W. BANNER
Commissioner of Patents and Trademarks